US008147857B2

(12) United States Patent
Fugmann et al.

(10) Patent No.: US 8,147,857 B2
(45) Date of Patent: Apr. 3, 2012

(54) INFECTION-RESISTANT POLYURETHANE FOAMS, METHOD FOR PRODUCING THE SAME AND USE THEREOF IN ANTISEPTIC WOUND DRESSINGS

(75) Inventors: Burkhard Fugmann, Ratingen (DE); Melita Dietze, Erkrath (DE)

(73) Assignee: Bayer Innovation GmbH, Dusseldorf (DE)

( * ) Notice: Subject to any disclaimer, the term of this patent is extended or adjusted under 35 U.S.C. 154(b) by 653 days.

(21) Appl. No.: 11/722,284

(22) PCT Filed: Dec. 13, 2005

(86) PCT No.: PCT/EP2005/013340
§ 371 (c)(1),
(2), (4) Date: Jun. 20, 2007

(87) PCT Pub. No.: WO2006/066752
PCT Pub. Date: Jun. 29, 2006

(65) Prior Publication Data
US 2010/0021514 A1    Jan. 28, 2010

(30) Foreign Application Priority Data
Dec. 21, 2004  (DE) .......................... 10 2004 061 406

(51) Int. Cl.
*A61K 9/70* (2006.01)
*A61K 31/785* (2006.01)
(52) U.S. Cl. .................... 424/409; 424/78.06; 604/304; 604/360; 604/368
(58) Field of Classification Search .................. None
See application file for complete search history.

(56) References Cited

U.S. PATENT DOCUMENTS

| 4,466,936 A | 8/1984 | Schapel |
| 4,479,795 A | 10/1984 | Mustacich et al. |
| 4,643,181 A | 2/1987 | Brown |
| 4,661,099 A | 4/1987 | von Bittera |
| 5,451,424 A | 9/1995 | Solomon et al. |
| 5,869,073 A | 2/1999 | Sawan et al. |
| 2002/0187176 A1* | 12/2002 | Yao ............................... 424/405 |
| 2004/0018227 A1 | 1/2004 | Park et al. |
| 2004/0028722 A1 | 2/2004 | Serafica et al. |
| 2005/0100588 A1 | 5/2005 | Kartheus |

FOREIGN PATENT DOCUMENTS

| DE | 139942 | 1/1980 |
| DE | 31 03 499 | 8/1982 |
| DE | 31 03 500 | 8/1982 |
| EP | 0 147 588 | 7/1985 |
| EP | 0106439 | 11/1987 |
| EP | 288865 A2 | 4/1988 |
| EP | 1175148 | 3/2003 |
| GB | 2085454 | 4/1982 |
| GB | 2170713 A | 8/1986 |
| GB | 2290031 | 12/1995 |
| WO | WO 88/01877 | * 3/1988 |
| WO | WO 94/07935 | 4/1994 |
| WO | WO 96/22114 | 7/1996 |
| WO | WO 97 00076 | 1/1997 |
| WO | WO 97/05910 | 2/1997 |
| WO | WO 99/40791 | 8/1999 |
| WO | WO 02/03899 | 1/2002 |
| WO | WO 02/100450 | 12/2002 |
| WO | WO 03/066116 | 8/2003 |

OTHER PUBLICATIONS

Howard et al.: Pharmaceutical Dosage forms and Drug Delivery Systems. 7th edition, (Lippincot Williams & Wilkins, A Wolters Kluwer Company, 1999), pp. 165, 166, and 170.*
International Search Report, PCT/EP2005/013340, dated Apr. 13, 2006.
3.4 Hilfs-und Zusatzstoffe fur Polyurethane, Literatur S. 125, plus English translation "3.4.4.3 Cell Regulators".
High Polymers, vol. XVI, "Polyurethanes, Chemistry and Technology" (Saunders-Frisch, Interscience Publishers, New York, vol. 1, 1962, pp. 32-34).
Absorbent Polymer Technology (Brannon-Peppas, Harland, Elsevier, Amsterdam-Oxford-New York-Tokyo, 1990, pp. 9-22.
Becker/Braun, Kunststoff-Handbuch, vol. 7, Polyurethane, $3^{rd}$ ed., Carl-Hauser Verlag Munich Vienna, 1993.

* cited by examiner

*Primary Examiner* — Ernst Arnold
*Assistant Examiner* — Hong Yu
(74) *Attorney, Agent, or Firm* — Baker, Donelson, Bearman, Caldwell & Berkowitz, P.C.

(57) ABSTRACT

The present invention describes microbicidal hydrophilic polyurethane foams endowed with polyhexamethylenebiguanide (PHMB) and/or its hydrochloride and also a superabsorbent, wound contact materials obtainable therefrom and processes for producing the therapeutically endowed polyurethane foams and the wound contact materials obtainable therefrom.

14 Claims, No Drawings

INFECTION-RESISTANT POLYURETHANE FOAMS, METHOD FOR PRODUCING THE SAME AND USE THEREOF IN ANTISEPTIC WOUND DRESSINGS

CROSS REFERECE TO RELATED APPLICATIONS

The present application is a 35 U.S.C. §371 National Stage Application of International Application No. PCT/EP2005/013340, having an international filing date of Dec. 13, 2005, and claiming priority to DE 102004061406.7 filed Dec. 21, 2004.

BACKGROUND OF THE INVENTION

1. Field of the Invention

The present application relates to an infection-resistant polyurethane foam, in particular a hydrophilic polyurethane foam, in which the antiseptic polyhexamethylenebiguanide (PHMB) and/or its hydrochloride is present in the PU foam layer in microparticulate and/or homogeneously dissolved form as well as a superabsorbent, a process for its production and its use in wound contact materials.

2. Description of Related Art

There is a general commitment in medicine to use infection-resistant materials to achieve the best possible control of infections on contact of exogenous material with injured tissue or with bodily fluids. Owing to their versatile properties and flexible shaping, polymeric materials of construction which have been rendered infection-resistant are particularly suitable for the fabrication of medical devices or ancillary equipment.

U.S. Pat. No. 4,479,795 A describes medical equipment composed of permeable polymers containing releasable microbicidal substances capable of diffusing to the surface of the polymer, in particular carboxylic acids.

U.S. Pat. No. 5,451,424 A describes a method of preparing a medical article from a homogeneous polymeric melt, in particular polyurethane or polyurethane-siloxane block copolymers, and chlorhexidine.

WO 96/22114 A describes a medical device comprising polyurethane as a polymeric material in which a microbicidal agent, triclosan, is present as a plasticizer at up to 30% by weight in a homogeneous solution. The polyurethane described is produced by blending a polyurethane resin with the triclosan.

GB 2085454 A describes the use of a microbicidal comonomer to make a microbicidal polymer.

A microbicidal polymeric material for producing medical equipment comprising PHMB as a microbicidal agent which is present in the polymeric carrier in microparticulate form is not described in this context.

Large or chronic wounds are particularly prone to become infected. Antiseptic polymeric wound contact materials shall prevent infections in a reliable and skin-compatible manner and thereby provide sustained support for the healing process.

WO 03/066116 A1=US 2003/0149406 A1 describes multilayered polymeric wound dressings composed of polyurethane foam, preferably of HYPOL, in which therapeutically acting substances can be incorporated. At least one of the layers is a hydrogel to cover the wound. The active ingredient or ingredients are dispersed in the polymeric carrier or enclosed in micelles. Release of the therapeutic ingredient from the micelles is limited to the micelles close to the surface.

US 2004/0018227 A1 describes three-layered wound dressing consisting inter alia of a porous polyurethane foam capable, through physical action as a sponge, of taking up wound exudate. The polyurethane mass may contain antibacterial substances and growth factors. Superabsorbents useful as a moisture-binding constituent are not mentioned, nor are any examples provided as to how antibacterial substances or growth factors can be incorporated in the polyurethane.

EP 1 175 148 A1 claims polymeric wound contact materials composed of PU foams in whose structure the antiseptic, including PHMB, is chemically bound to the polymeric structure through covalent bonding. Here, the covalent bonding to the supporting PU foam means that bioavailability is only limited.

EP 0 106 439 A1 and GB 2 290 031 A1 describe multilayered polymeric wound contact materials comprising a polyurethane foam interlayer in which the therapeutically acting substances can be incorporated by impregnation, for example, although there is no detailed description as to the form in which the therapeutically acting substances are present and to what extent they are available to the wound to be treated.

GB 2 170 713 A1 describes explicitly microporous PU foams useful as wound contact materials which are impregnated through the action of absorbing an antiseptic solution; here, the therapeutic is only temporarily available until it is flushed out by wound exudate for example.

WO 02/100450 A1 describes medicated polyurethane gels, optionally in the form of a foam, for use on skin and/or wounds, the gels containing an active ingredient for transdermal application which is present in homogeneous form.

DD 139942 describes a process for producing single-layered PU foam wound contact materials having an antibacterial or some other therapeutic effect; however, the process always appears to require the addition of a hydrophilic substance other than the active component, for example carbohydrates in proportions of 1-50% or some other granulation-promoting hydrophilic agent.

PHMB has been widely described in the literature as an antiseptic agent.

WO 99/40791 A1 describes for example a water-insoluble, transparent, adherent, antimicrobial film which is applied to surfaces and has both a short-term and a long-term disinfecting effect. The antimicrobial film comprises an organic biguanide polymer and also antimicrobial metallic material.

U.S. Pat. No. 5,869,073 A1 describes a liquid composition for surface coating. The liquid composition consists of a solution, dispersion or suspension of a biguanidic polymer and antimicrobial metallic material.

The additional use of the biocidal metallic material makes the fabrication of the wound contact materials obtained therefrom inconvenient and costly.

US 2004/0028722 A1 and WO 02/03899 A1 describe a cellulose wound dressing for chronic wounds which contains antimicrobial additives, for example PHMB. Cellulose as a carrier material has the disadvantage of tending to stick to the wound, and this makes changing the dressing inconvenient and may impair the healing process.

WO 97/05910 A1 describes cellulose material containing a mixture of PHMB and of an anionic polymer such as polyacrylic acid superabsorbent for example. The material described is used in diapers and sanitary napkins, there is no mention of a use in the sector of wound management.

U.S. Pat. No. 4,643,181 A describes a surgical dressing comprising a substrate coated with an antimicrobial adhesive layer. The antimicrobial agent is PHMB in certain particle sizes. The presence of PHMB in the adhesive layer, however, cannot preclude the possibility of the rest of the dressing material being colonized by bacteria.

Similarly, WO 88/01877 A1 describes a hydrophilic PU wound dressing comprising a hydrophilic gel-adhesive layer which may contain active antimicrobial ingredients as well as other ingredients. Hydrogelic adhesive layers generally have but a very limited capacity for taking up wound exudate. Since, frequently, a polymeric foam layer has to be additionally included for this purpose, fabrication of the wound dressing becomes inconvenient and costly.

SUMMARY OF THE INVENTION

Proceeding from the prior art, it is accordingly an object of the present invention to produce a suitable microbicidal polymeric material for medical applications, in particular for the production of wound contact materials, which ensures an optimal and prolonged bioavailability of the antiseptic, is capable of taking up excess wound exudate in the process, permits air and moisture exchange and is simple and inexpensive to fabricate.

The present invention accordingly provides cellular hydrophilic polyurethane gels containing PHMB or PHMB hydrochloride and also a superabsorbent, characterized in that the PHMB and/or the PHMB hydrochloride is present in the polyurethane gel as a microparticulate dispersion and/or homogeneous solution.

DETAILED DESCRIPTION OF A PREFERRED EMBODIMENT

A cellular polyurethane gel is for example a polyurethane gel foam which shall be closed- or open-cell, preferably open-cell. Foam pore sizes vary in general between 10 and 2000 μm, preferably 50 and 500 μm.

As used herein, microparticulate dispersion is to be understood as meaning a substantially uniform dispersion of substance dispersed in the carrier material in finely ground or micronized form. The particle size is generally on the order of 0.5 to 50 μm, preference being given to using particles of 1 to 5 μm.

The substantially homogeneous microparticulate dispersion or solution of the PHMB or PHMB hydrochloride in the present invention's carrier material in the presence of the superabsorbent provides a high uptake capacity with regard to fluid, in particular wound fluid, coupled with a simultaneous microbicidal effect which occurs immediately and/or lasts over a period of 1 to 30 days, preferably 2 to 15 days and more preferably 5 to 7 days. The uptake capacity for any one fluid generally varies greatly with the composition of the fluid, among other factors, from 1 to 15 times and preferably from 2 to 10 times the weight of the present invention's polyurethane gel.

When the present invention's polyurethane gel foam is used as a wound contact material, it is a characteristic feature that the germ-containing wound exudate is taken up in the polyurethane foam material never to be released back into the wound, resulting in a distinct effect enhancement in relation to germ control over the prior art coupled with surprisingly low concentrations of the microbicide in the carrier material and a broad spectrum of germs.

The use of the present invention's polyurethane gel foam in a wound contact material has the advantages that an instant effect and, beyond that, a long-term effect over several days facilitates the re-formation of tissue without this being compromised by frequent changes of the dressing. Combined with the ideally moist medium due to the combination of the foam structure of the polyurethane gel carrier with the absorbent effect of the superabsorbent for taking up wound fluid, the result is a good healing environment. Fixing and killing the germs in the polyurethane foam protects the wound successfully against reinfection. A further enhancement of the healing success is conceivable through possible addition of one or more further actives and/or through addition of enzymes, growth factors or else cell implants from skin or stem cells, which may optionally also be present in the additional layers of a wound contact material. The patient's well-being is enhanced by the skin-friendly hydrophilic elastic polyurethane foam material and/or by local anesthetics additionally included in the carrier material for pain relief. The foam structure of the wound dressing provides thermal insulation to a wound.

Useful polymeric materials include for one particularly hydrophilic polyurethane foam gels constructed of nonaromatic isocyanates and a) polyetherpolyols with 2 to 6 hydroxyl groups and having OH values of 20 to 112 and an ethylene oxide (EO) content of ≧10% by weight,
b) antioxidants,
c) catalysts,
d) hexamethylene diisocyanate or a modified hexamethylene diisocyanate,
e) antimicrobial actives,
f) superabsorbent,
g) foaming agent, wherein the product of the functionalities of the polyurethane-forming components a) and d) is at least 5.2, the catalyst quantity c) is 0.005% to 0.5% by weight based on the polyol a), the amount of antioxidants b) is at least 0.1% by weight based on polyol a) and a ratio of free NCO groups in component d) to the free OH groups in component a) (isocyanate index/100) is selected in the range from 0.30 to 0.70, and the amount of active e) is 0.0001% to 25% by weight, preferably 0.001% to 5% by weight and more preferably 0.01-1% by weight, based on the polyol a). The isocyanate index (K, ratio of the free NCO groups used in the reaction to the free OH groups×100) of the present invention's polyurethane gel materials varies with the functionality of the employed isocyanate components ($F_I$) and polyol components ($F_P$) in the range from 30 to 70 and preferably in the range from 45 to 60. The isocyanate index required for gel formation is very simple to estimate using the following formula:

$$K \approx \frac{F_I}{F_P \cdot (F_I - 1)} \times 100$$

Depending on the tackiness and elasticity desired for the gel, the actual isocyanate index to be used can differ from the calculated value by up to ±20%. The amount of superabsorbent f) is 0.1-50% by weight, preferably 2-30% by weight and more preferably 25-29% by weight based on the sum total of the polyurethane-forming components a) and d).

The present invention's polyetherpolyols a) are known per se and are for example prepared by polymerization of epoxides, such as ethylene oxide, propylene oxide, butylene oxide or tetrahydrofuran, with themselves or by addition of these epoxides, preferably ethylene oxide and propylene oxide—if appropriate mixed with each other or separately from each other—onto starter components having at least two reactive hydrogen atoms, such as water, ethylene glycol, propylene glycol, diethylene glycol, dipropylene glycol, glycerol, trimethylolpropane, pentaerythritol, sorbitol or sucrose. Representatives of the aforementioned high molecular weight polyhydroxy compounds to be used are recited for example in High Polymers, Vol. XVI, "Polyurethanes, Chemistry and Technology" (Saunders-Frisch, Interscience Publishers, New York, Vol. 1, 1962, pages 32-34). In accordance with the present invention, polyetherpolyols are preferred which have 3 to 4 and more preferably 4 hydroxyl groups and an OH number in the range of 20-112, preferably 30-56. The ethylene oxide content of the polyetherpolyols used according to the present invention is preferably $\geq$20% by weight.

Isocyanate component d) comprises monomeric or trimerized hexamethylene diisocyanate or hexamethylene diisocyanate modified by biuret, uretidione, allophanate groups or by prepolymerization with polyetherpolyols or mixtures of polyetherpolyols based on the familiar starter components having at least two reactive hydrogen atoms and epoxides, such as ethylene oxide or propylene oxide of OH number $\leq$850, preferably 100 to 600. Preference is given to the use of modified hexamethylene diisocyanate, in particular by prepolymerization with polyetherdiols of OH number 200 to 600, whose residual level of monomeric hexamethylene diisocyanate is below 0.5% by weight.

Useful catalysts c) include those active for the reaction between hydroxyl and isocyanate groups, preferably those which are generally known in polyurethane chemistry. Illustrative catalysts used are tertiary amines, such as triethylamine, N-tetramethylethylenediamine, 1,4-diazabicyclo-[2,2,2]octane, N,N-dimethylbenzylamine, N-methyl-N'-dimethylaminoethylpiperazine, pentamethyldiethylenetriamine, or else Mannich bases known as catalysts and formed from secondary amines, such as dimethylamine and aldehydes (formaldehyde) or ketones (acetone) and phenols, or silaamines having C—Si bonds, such as 2,2,4-trimethyl-2-silamorpholine and 1,3-diethylaminomethyltetramethyldisiloxane. Useful catalysts further include organic metal compounds, in particular tin compounds, such as tin(II) acetate, tin(II) ethylhexanoate, tin(IV) compounds such as for example dibutyltin dichloride, dibutyltin dilaurate, dibutyltin maleate, bismuth(III) carboxylates which are soluble in the anhydrous polyetherpolyols a) and are based on linear, branched, saturated or unsaturated carboxylic acids having 2 to 18 and preferably 6 to 18 carbon atoms. Preference is given to Bi(III) salts of branched saturated carboxylic acids having tertiary carboxyl groups, such as 2,2-dimethyloctanoic acid (for example Versatic acids, Shell). Of particular suitability are formulations of these Bi(III) salts in excess proportions of these carboxylic acids. Of outstanding utility is a solution of 1 mol of the Bi(III) salt of Versatic 10 acid (2,2-dimethyloctanoic acid) in an excess of 3 mol of this acid with a Bi content of about 17%. (Bi(III) neodecanoate, Coscat 83 from Brenntag NV). Further suitable catalysts are described in German Laid-Open Specification 29 20 501 at page 29 line 5 to page 31 line 25.

The catalysts are preferably used in amounts of 0.03% to 0.2% by weight, based on the polyol a).

Useful antioxidants b) for the present invention's polyurethane gels are in particular sterically hindered phenolic stabilizers, such as BHT (2,6-di-tert-butyl-4-methylphenol), Vulkanox BKF (2,2'-methylenebis(6-tert-butyl-4-methylphenol) (Lanxess), Irganox 1010 (pentaerythrityl tetrakis [3-(3,5-ditert-butyl-4-hydroxyphenyl)propionate]), Irganox 1076 (octadecyl-3-(3,5-ditert-butyl-4-hydroxyphenyl)propionate) (Ciba Specialty Chemicals) or tocopherol (vitamin E). Preference is given to using those of the α-tocopherol type. Further stabilizers are mentioned for example in Ullmann (5th edition, Volume A3, pages 91-111; Volume A20, pages 461-479; Volume A23; pages 381-391). The stabilizing properties of the phenolic stabilizers can be further enhanced by addition of organically substituted sulfides or disulfides, for example Irganox PS800 (dilauryl 3,3'-thiopropionate) or dioctyl didecyl disulfide. Combinations of the phenolic types with one another are also possible.

The antioxidants are preferably used in amounts of 0.1% to 2.0% by weight are especially 0.15% to 0.5% by weight, based on the polyol a). In the case of antioxidant mixtures as mentioned above, the antioxidants are preferably used in amounts of 0.05% to 0.5% by weight per individual substance, based on the polyol a).

As actives e), the present invention's polyurethane gel foams utilize at least one antiseptic, preferably polyhexamethylenebiguanide (PHMB) or its salts, more preferably the hydrochloride of PHMB, but also additionally other actives from the group of the broad spectrum antibiotics, the antimicrobial actives, the antifungal actives, the antipathogenic peptides, the local anesthetics, the actives having an antiseptic, hemostatic, wound-healing, immunomodulatory or granulation-promoting effect or an effect on the central nervous system, the enzymes, in particular those having an antibacterial effect, for example lysozyme, papain, trypsin, bactilysin, glucose oxidase), the growth factors, in particular epidermal growth factor (EGF), platelet derived growth factor (PDGF), transforming growth factor alpha/beta (TGF), insulin-like growth factor (IGF, ILGF), fibroblast growth factor (FGF), vascular endothelial growth factor (VEGF), blood-derived growth factor (BDGF), tissue growth factor or growth- and amelogenin-like factors (GAF) are used singly or in combination.

Useful broad-spectrum antibiotics include in particular fosfomycin, gentamicin or mupirocin and also antibacterial quinolonecarboxylic acids, useful antivirals include in particular the nucleoside-analogous virustats such as aciclovir, ganciclovir, vidarabin, zidovudin or else foscarnet, useful antifungals include in particular the azole antimycotics such as fluconazole, clotrimazole or itraconazole and the allylamines such as terbinafin or morpholines such as amorolfin or polyenes such as natamycin, useful antipathogenic peptides include for example lysozyme, the local anesthetics for example lidocaine, benzocaine, bupivacaine or procaine. Very particular preference is given to using polyhexamethylenebiguanide hydrochloride alone.

Superabsorbents f) are known water-absorbing salts of polyacrylates and copolymers thereof, in particular the sodium and potassium salts. They can be crosslinked or uncrosslinked and are also commercially available. Particularly suitable products are those disclosed in DE 37 13 601 A1 and also new-generation superabsorbents with only low remaining contents of water which can be dried out and high swelling capacity under pressure. Particularly preferred products are lightly crosslinked polymers based on acrylic acid/ sodium acrylate. These are obtainable as Favor T (Degussa AG). Further absorbents are likewise suitable, examples being carboxymethylcellulose and karaya.

Useful foaming agents g) include foaming agents common in polyurethane chemistry. They include for example carbon dioxide created chemically in situ as reaction product of isocyanate with water, or physically acting, water-free blowing agents such as low-boiling liquids, examples being fluorocarbon 113, hydrofluorochlorocarbon 22, n-pentane, isopentane, cyclopentane, butanes and hexanes. Further ones are described for example in Becker/Braun, Kunststoff-Handbuch, Volume 7, Polyurethane, 3rd edition, Carl Hanser Verlag Munich-Vienna, 1993, pages 115-118. However, inert gases are particularly useful for foaming the present invention's polyurethanes. In this technique, gases, for example nitrogen, noble gases or carbon dioxide, are incorporated by means of commercially available polyurethane mixing technology without addition of water.

The degree of foaming can be varied within wide limits through the incorporated amounts of foaming agent.

The present invention's polyurethane gel compositions are prepared in conventional processes, as described for example in Becker/Braun, Kunststoff-Handbuch, Volume 7, Polyurethane, 3rd edition, Carl-Hauser Verlag Munich Vienna, 1993 pages 139 ff. The reaction can be carried out in various ways, as also described therein. Preference is given to taking 1-10% of the total amount of polyol a), which contains antioxidants b), and dissolving or dispersing therein the catalyst here referred to as mixture A). The remainder of the polyol a) is mixed with the active or actives e) and superabsorbent f) to form the mixture B). The reaction can then be carried out by initially mixing the mixtures A) and B) and then adding the isocyanate mixture, in this case the optionally modified hexamethylene diisocyanate, d). In the process, the present invention's hydrophilic polyurethane gels are foamed in the course of the reaction by direct addition of the foaming agent g) as a gas or liquid, the density of the foamed gel reducing down to ⅙ of the initial density of the gel mass and the volume increasing accordingly. It is also possible to combine all constituents A), B), d) and g) at the same time. When low-boiling liquids are used, these are preferably mixed with one of the components A), B) or d). A broadly applicable description is to be found in WO 94/07935 A1 at page 19 line 9 to page 22 line 18.

It is further possible to use preferably hydrophilic polyurethane gel foams consisting of a polyurethane gel which is self-adhesively or alternatively non-adhesively elastic and which contains (A) 25-62% or alternatively 15-62% by weight, preferably 30-60% or alternatively 20-57% by weight, more preferably 40-57% or alternatively 25-47% by weight, based on the sum total of (A) and (B), of a covalently crosslinked polyurethane as a high molecular weight matrix and (B) 75-38% or alternatively 85-38% by weight, preferably 70-40% or alternatively 80-43% by weight, more preferably 60-43% or alternatively 75-53% by weight, based on the sum total of (A) and (B), of one or more polyhydroxy compounds which are firmly held in the matrix by secondary valence forces and have an average molecular weight between 1000 and 12 000, preferably between 1500 and 8000, more preferably between 2000 and 6000, and an average OH number between 20 and 112, preferably between 25 and 84 and more preferably between 28 and 56, as a liquid dispersant, the dispersant being substantially free of hydroxy compounds having a molecular weight below 800, preferably below 1000 and more preferably below 1500, and also (C) 0.00001% to 25% by weight, preferably 0.001% to 5% by weight and more preferably 0.001-2.5%, based on the sum total of (A) and (B), of active, preferably polyhexamethylenebiguanide, more preferably its hydrochloride, and if appropriate one or more further actives and also (D) 0.1% to 50% by weight, preferably 2-30% by weight and more preferably 25-29% by weight, based on the sum total of (A) and (B), of superabsorbent (E) 0.01% to 10% by weight based on the sum total of (A) and (B) of foaming agent, and also if appropriate (F) 0% to 100% by weight, based on the sum total of (A) and (B), of filler and/or additive substances, and which is obtainable by reaction of a mixture of I) one or more polyisocyanates, II) one or more polyhydroxy compounds having an average molecular weight between 1000 and 12 000 and an average OH number between 20 and 112, III) one or more antimicrobial actives, IV) one or more water-absorbing materials, V) a foaming agent which is liquid or gaseous at room temperature, and also if appropriate VI) catalysts and accelerants for the reaction between isocyanate groups and hydroxyl groups, and also if appropriate VII) filler and additive substances known per se from polyurethane chemistry, wherein the mixture is substantially free of hydroxy compounds having a molecular weight below 800, the average functionality of the polyisocyanates ($F_I$) is preferably between 2 and 4, the average functionality of the polyhydroxy compound ($F_P$) is between 3 and 6 and the isocyanate index (K) conforms to the formula $$K = \frac{300 \pm X}{(F_I \cdot F_P) - 1} + 7$$

where X is $\leq 120$, preferably X is $\leq 100$ and more preferably X is $\leq 90$ and the K index has values between 50 and 70, the specified molecular weight and OH number averages being number averages.

The polyurethane gels are obtainable from the starting compounds known per se from polyurethane chemistry by processes known per se as described for example in DE 31 03 499 A1, DE 31 03 500 A1 and EP 0 147 588 A1. It is essential, however, that the above-defined conditions be adhered to for the selection of the gel-forming components to differentiate the properties of the desired gels in order that non-adhesive elastic gels are obtained in one case or alternatively self-adhesive gels are obtained.

Preferred polyhydroxy compounds are polyether polyols as more particularly specified in the abovementioned Laid-Open Specifications.

Useful polyisocyanate components I) include not only (cyclo)aliphatic but also aromatic isocyanates. Preferred (cyclo)aliphatic polyisocyanates are 1,6-hexamethylene diisocyanate and also its biurets and trimers and hydrogenated diphenylmethane diisocyanate ("MDI") grades. Preferred aromatic polyisocyanates are those which are obtained by distillation, such as MDI mixtures of 4,4'- and 2,4'-isomers or 4,4'-MDI and also tolylene diisocyanate ("TDI") grades. The TDI grades may also contain higher functional fractions due to modifications, such as biuretization or trimerization. The diisocyanates characterizing the polyisocyanates can be selected in particular for example from the group of the unmodified aromatic or aliphatic diisocyanates or alternatively from modified products formed by prepolymerization with amines, polyols or polyetherpolyols.

Useful polyhydroxy compounds II) include the materials indicated at a) above in the description of the polyurethane foam gels constructed from nonaromatic isocyanates.

Useful active III) include those indicated, preferred and particularly preferred at e) in the above description of the polyurethane foam gels constructed from nonaromatic isocyanates. Very particular preference is given to using polyhexamethylenebiguanide hydrochloride alone.

Useful water-absorbing materials IV) preferably include the superabsorbent at f) in the above description of the polyurethane foam gels constructed from nonaromatic isocyanates, preferably the superabsorbents preferred at f).

Useful foaming agents V) include those common in polyurethane chemistry which are indicated at g) in the above description of the polyurethane foam gels constructed from nonaromatic isocyanates. Depending on their properties, these foaming agents will be present in the final polyurethane foam in a dissolved state.

Useful catalysts and accelerants VI) for the reaction between isocyanate groups and hydroxyl groups include if appropriate those indicated at c) in the above description of the polyurethane foam gels constructed from nonaromatic isocyanates.

Useful filler and additive materials VI) include the additive materials known per se from polyurethane chemistry. Such additive materials include if appropriate the antioxidants mentioned in the above description of the polyurethane foam gels constructed from nonaromatic isocyanates. In accordance with the present invention, the hydrophilic materials of foam gel may have added to them, preferably at up to 100% by weight, based on the total weight of the gel, fillers, dyes, metal pigments, thickening agents, surface-active substances, extenders, resins, etc. Useful inorganic fillers include in particular powders composed of zinc oxide, titanium dioxide, barite, chalk, gypsum, kieserite, sodium carbonate, cerium oxide, quartz sand, kaolin, carbon black and micro-balloons and also short fibers, such as glass fibers 0.1-1 mm in length. As organic fillers there may be recited in particular powders based on polystyrene, polyvinyl chloride, urea-formaldehyde and polyhydrazodicarbonamide, swellable powders and fibers <0.01 mm in fiber length, for example fibers based on polyacrylic acids and their salts or others, as mentioned for example in Absorbent Polymer Technology (Brannon-Peppas, Harland, Elsevier, Amsterdam-Oxford-New York-Tokyo, 1990, pages 9-22), and also materials used as textile fibers, examples being polyester or polyamide fibers. Useful dyes or color pigments include in particular those used in foods, packaging or cosmetics, such as iron oxide or chromium oxide pigments, pigments based on phthalocyanine or on a monoazo basis. Useful surface-active substances include for example cellulose powder, activated carbon and silica products.

To modify the adhesive properties of the gels, they may optionally include additions of extenders and resins, i.e. polymeric vinyl compounds, polyacrylates and other copolymers customary in adhesive technology, or else adhesives based on natural materials, at up to a level of 10% by weight, based on the weight of the gel composition.

The present invention's polyurethane gel compositions are prepared in conventional processes as described for example in Becker/Braun, Kunststoff-Handbuch, Volume 7, Polyurethane, 3rd edition., Carl-Hauser Verlag Munich Vienna, 1993 pages 139 ff. The reaction can be carried out, as also stated there, using different procedures and different machines.

The present invention's polyurethane foam gel compositions can be used generally for producing medical equipment, in particular shaped articles and adhesive layers, preferably products having contact with human and animal tissues, as with the skin, with mucosae, or with open wounds or with bodily fluids and secretions/exudates, as for example saliva, blood, wound fluids, urine, feces or perspiration. The materials are also useful for adhering and fixing to skin.

Preference is given to using the present invention's polyurethane foam gel compositions in the wound management sector, in particular as a weakly or strongly self-adhering or else non-adhering elastic at least single-ply layer, used as plasters, quick wound bandages, as a wound contact material for large or chronic wounds, for example burn injuries, or for adhering wound management products to a body's surface. They additional serve to take up blood or wound exudate and also for cushioning and thermal insulation. Further fields of use include for example orthopedic articles, hygiene and cosmetic articles or strongly moisture-absorbing, swellable and cushioning pads and inserts, for example shoe inserts, if appropriate also as pressure-distributable filling compositions for cushions or cushioning elements.

The present invention's polymer and its use in wound contact materials make for example the following advantages possible:

Control of microbial infection of the wound and prevention of reinfection

Absorption and irreversible retention of wound exudate and hence support of the healing process Killing bacteria absorbed in the foam together with wound exudate Skin compatibility of the polyurethane material The frequent changing of the wound contact material (several times a day at present) becomes superfluous, leaving the contact material on the wound for at least 3 up to 5 days becomes possible, and so new skin tissue is able to form better without disruption.

Thermal insulation of a wound

Further actives such as antibiotics for assisting bacterial control or local anesthetics for pain alleviation can be incorporated in the polymer and slowly released again continuously therefrom.

If appropriate acceleration of wound healing through enzymes, growth factors and cell implants (stem cells for example).

Conceivable wound contact materials fabricated from the present invention's polymer consist at least of the infection-resistant polyurethane foam which contains an antiseptic, preferably PHMB, and superabsorbent and is self-adhesive if appropriate and if appropriate comes into direct contact with the wound, and also optionally a further adhesive layer for fixing the wound contact material to the skin and also optionally an air- and externally moisture-pervious polymer film covering of, for example, polyurethane for mechanical protection and handling of the wound contact material and also to protect the present invention's polyurethane foam against the ingress of moisture and microorganisms.

The optional adhesive layer for fixing the infection-resistant polyurethane foam can in turn be optionally endowed with antimicrobial, preferably PHMB or pain-relieving substances. The present invention's polyurethane foam can if appropriate be coated on the wound side with a layer of various materials, examples being collagen, alginates, hydrocolloids, hydrogels, hydrofibers, a cellulose fleece, a pervious silicone layer, a synthetic (polyurethane) polymer or inorganic silica gel fiber polymers which can in turn contain wound healing promoters, analgesics, antiseptics, antibiotics, enzymes, growth factors or cells. The materials allow moisture to pass into the present invention's polyurethane foam. This additional layer can for example like the exudate-absorbing foam likewise contain PHMB, which is capable of controlling bacteria in direct contact with the wound, and ensures the accelerated recurrence of the effect mediated by the present invention's polyurethane foam. This additional layer can serve as particularly skin-friendly, atraumatic surface for the present invention's polyurethane foam when the wound is particularly sensitive.

The described assembly of various layers in the wound contact material can be enclosed in a filmlike material to form a sterile package, the package being opened directly before use.

The construction of such wound contact materials is common knowledge and described for example in WO 02/100450 A1 and shown therein in FIGS. 1 to 6.

Preference, particular preference or very particular preference is given to embodiments utilizing parameters, compounds, definitions and elucidations mentioned under preferred, particularly preferred or very particularly preferred.

The general or preferred definitions, parameters, compounds and elucidations recited in the description, however, may also be combined with one another, i.e. between the respective ranges and preferred ranges, in any desired way.

The example which follows is intended to particularly elucidate the invention without, however, restricting the invention thereto.

EXAMPLE

Example 1

In a paperboard cup, 64.22 g of Levagel® SN 100 [Bayer MaterialScience AG, polyol interpolymer of propylene oxide and ethylene oxide (EO), pentaerythritol starter, ethylene oxide end block, OH number 4, average molecular weight 6400, EO content 20% by weight, stabilized with 0.5% by weight of 2,6-di-tert-butyl-4-methylphenol (BHT)] are admixed with 27.52 g of FAVOR®-PAC 230 (Degussa AG, superabsorbent based on polyacrylic acid, salt of a crosslinked grafted polyacrylic acid-polyalcohol copolymer) and 1.00 g of PHMB hydrochloride, previously supplementarily dried at 80° C. in a vacuum drying cabinet, by stirring. This is followed by addition of a freshly prepared solution of 0.055 g of dibutyltin laurate in 2.70 g of Levagel® SN 100 and thorough commixing. Lastly, 5.505 g of Desmodur® E 305 (Bayer MaterialScience AG, NCO-terminated prepolymer based on 7 mol of hexamethylene diisocyanate and 1 mol of polypropylene oxide and having an average molecular weight of 400 g/mol, NCO content about 12.3-13.3% by weight) and 5 g of isopentane are added, followed by commixing for 1 min, and pouring of the mass into a Teflon dish. A pale yellow tacky foam is obtained.

The invention claimed is:

1. A cellular hydrophilic polyurethane gel containing an antiseptic agent polyhexamethylenebiguanide or a hydrochloride thereof, a superabsorbent, at least one therapeutic agent, wherein the antiseptic agent is present in the polyurethane gel as a microparticulate dispersion and/or homogenous solution and the at least one therapeutic agent is selected from the group consisting of broad-spectrum antibiotics, antimicrobial actives, antifungal actives, antipathogentic peptides, local anesthetics, actives having an antiseptic, hemostatic, wound-healing, immunomodulatory or granulation-promoting effect or an effect on the center nervous system.

2. A process for producing the cellular hydrophilic polyurethane gel according to claim 1 by reaction of monomers and a foaming agent in the presence of at least one of polyhexamethylenebiguanide or a hydrochloride thereof and the therapeutic agent, wherein at least one of polyhexamethylenebiguanide or a hydrochloride thereof and the therapeutic agent is mixed into a mixture of the monomers before polymerization.

3. A method for producing medical equipment comprising
   obtaining said cellular hydrophilic polyurethane gel according to claim 1; and
   fabricating said equipment with said cellular hydrophilic polyurethane gel.

4. A method for producing an at least one-ply wound contact material comprising
   obtaining said cellular hydrophilic polyurethane gel according to claim 1; and
   using said polyurethane to produce said cellular hydrophilic polyurethane gel.

5. A method for producing a wound contact material for large or chronic wounds comprising
   obtaining said cellular hydrophilic polyurethane gel according to claim 1; and
   using said polyurethane to produce said cellular hydrophilic polyurethane gel.

6. A wound contact material comprising said cellular hydrophilic polyurethane gel according to claim 1.

7. The cellular hydrophilic polyurethane gel according to claim 1, wherein the antiseptic agent is present as a microparticular dispersion comprising a substantially uniform dispersion of antiseptic agent, dispersed in the polyurethane gel in finely grounded or micronized form.

8. The cellular hydrophilic polyurethane gel according to claim 7, wherein the antiseptic agent is of particle size 0.5 to 50 μm.

9. The cellular hydrophilic polyurethane gel according to claim 7, wherein the antiseptic agent is of particle size 1 to 5 μm.

10. The cellular hydrophilic polyurethane gel according to claim 1, wherein the antiseptic agent is of particle size 0.5 to 50 μm.

11. The cellular hydrophilic polyurethane gel according to claim 1, wherein the antiseptic agent is of particle size 1 to 5 μm.

12. The cellular hydrophilic polyurethane gel according to claim 1, wherein the antiseptic agent is present as a particulate dispersion.

13. The cellular hydrophilic polyurethane gel according to claim 1, wherein the antiseptic agent is present as a homogeneous solution.

14. The wound contact material according to claim 6, further comprising a further adhesive layer for fixing the wound contact material to skin, and an air- and externally moisture-pervious polymer film covering of polyurethane.

* * * * *